(12) United States Patent
Bomsta

(10) Patent No.: US 11,517,225 B2
(45) Date of Patent: Dec. 6, 2022

(54) MULTI-PURPOSE DYNAMICALLY CONFIGURABLE BIOMETRIC PHOTONICS SENSOR PROBE

(71) Applicant: OWLET BABY CARE, INC., Lehi, UT (US)

(72) Inventor: Zack Bomsta, Provo, UT (US)

(73) Assignee: Owlet Baby Care, Inc., Lehi, UT (US)

( * ) Notice: Subject to any disclaimer, the term of this patent is extended or adjusted under 35 U.S.C. 154(b) by 216 days.

(21) Appl. No.: 16/054,548

(22) Filed: Aug. 3, 2018

(65) Prior Publication Data
US 2019/0038193 A1 Feb. 7, 2019

Related U.S. Application Data

(60) Provisional application No. 62/541,894, filed on Aug. 7, 2017.

(51) Int. Cl.
*A61B 5/1455* (2006.01)
*A61B 5/145* (2006.01)
*A61B 5/026* (2006.01)

(52) U.S. Cl.
CPC ...... *A61B 5/14551* (2013.01); *A61B 5/14542* (2013.01); *A61B 5/0261* (2013.01); *A61B 2562/0238* (2013.01)

(58) Field of Classification Search
CPC ............ A61B 5/14551; A61B 5/14542; A61B 5/0261; A61B 2562/0238
USPC ........................................................ 600/323
See application file for complete search history.

(56) References Cited

U.S. PATENT DOCUMENTS

| | | | |
|---|---|---|---|
| 4,407,290 A | 10/1983 | Wilber | |
| 4,807,630 A | 2/1989 | Malinouskas | |
| 6,711,424 B1 | 3/2004 | Fine et al. | |
| 6,778,923 B2 | 8/2004 | Norris et al. | |
| 7,894,869 B2 * | 2/2011 | Hoarau | A61B 5/14552 600/323 |
| 8,100,834 B2 * | 1/2012 | Shuler | A61B 5/7275 600/483 |
| 8,108,022 B2 | 1/2012 | Balberg et al. | |
| 8,391,979 B2 * | 3/2013 | Kuhn | A61B 5/02028 607/22 |
| 9,668,672 B2 | 6/2017 | Zalevsky et al. | |

(Continued)

OTHER PUBLICATIONS

Kenneth Humphreys et al. "Noncontact simultaneous dual wavelength photoplethysmography: A further step toward noncontact pulse oximetry," *Review of Scientific Instruments* vol. 78, (2007) pp. 044304-1-044304-6.

*Primary Examiner* — Daniel L Cerioni
*Assistant Examiner* — Deirdre M Willgohs
(74) *Attorney, Agent, or Firm* — Workman Nydegger P.C.

(57) ABSTRACT

A multi-purpose biometric sensor includes both a transmissive topology and reflective topology for measuring biometric information. The multi-purpose biometric sensor is configured to allow for dynamically switching between the transmissive topology and the reflective topology based on user input or a current measuring scenario. The multi-purpose biometric sensor includes multiple types of light emitting sources and is further configured to dynamically switch between different types of light emitting sources based on user input or a current measuring scenario. The multi-purpose biometric sensor is further configured to measure multiple biometric signals from a single sensor.

8 Claims, 3 Drawing Sheets

(56) References Cited

U.S. PATENT DOCUMENTS

| | | |
|---|---|---|
| 2009/0259116 A1 | 10/2009 | Wasserman et al. |
| 2013/0158413 A1* | 6/2013 | Lisogurski ......... A61B 5/14551 600/476 |
| 2015/0223700 A1* | 8/2015 | Kirenko ............. A61B 5/14551 600/476 |
| 2016/0345880 A1 | 12/2016 | Nakaji et al. |
| 2017/0281081 A1* | 10/2017 | Nousiainen ........ A61B 5/02427 |

* cited by examiner

MULTI-PURPOSE DYNAMICALLY CONFIGURABLE BIOMETRIC PHOTONICS SENSOR PROBE

CROSS-REFERENCE TO RELATED APPLICATIONS

This application claims the benefit of and priority to U.S. Provisional Patent Application Ser. No. 62/541,894 filed on Aug. 7, 2017, and entitled "MULTI-PURPOSE DYNAMICALLY CONFIGURABLE BIOMETRIC PHOTONICS SENSOR PROBE," which application is incorporated herein by reference in its entirety.

BACKGROUND

Many biometric applications today use photonic sensors that include one or more light emitting sources and one or more photo sensors to gather biometric information from the body. For instance, such biometrics may include heart rate, blood oxygen saturation, blood carbon monoxide saturation, blood flow rate, relative hydration levels, and so forth. Each biometric measurement may offer a separate, unique photonics sensor probe design. Such probe designs generally comprise one of two common photonic sensor topologies—transmissive and reflective. Both of these topologies include advantages and disadvantages in a wide variety of monitoring scenarios. However, existing probe designs use only one of the two topologies, thus forcing users to accept the advantages/disadvantages associated with a chosen topology.

Additionally, numerous types of light emitting sources may be used for biometric probe designs. However, existing probe designs include only one type of light emitting source, again forcing users to accept the advantages/disadvantages associated with a chosen light emitting source.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Embodiments disclosed herein comprise apparatus configured to measure biometric information using either or both of a transmissive topology and a reflective topology within the same biometric sensor. In particular, disclosed embodiments comprise multi-purpose biometric sensors that are configured to allow for dynamically switching between a first topology (e.g., a transmissive topology) and a second topology (e.g., a reflective topology) in accordance with user input or a current measuring scenario. The multi-purpose biometric sensors are further configured to dynamically switch between different types of light emitting sources based on user input or a current measuring scenario. The multi-purpose biometric sensors are also configured to measure multiple biometric signals from a single sensor.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Embodiments disclosed herein comprise apparatus configured to measure biometric information using either or both of a transmissive topology and a reflective topology within the same biometric sensor. In particular, disclosed embodiments comprise multi-purpose biometric sensors that are configured to allow for dynamically switching between a first topology (e.g., a transmissive topology) and a second topology (e.g., a reflective topology) in accordance with user input or a current measuring scenario. The multi-purpose biometric sensors are further configured to dynamically switch between different types of light emitting sources based on user input or a current measuring scenario. The multi-purpose biometric sensors are also configured to measure multiple biometric signals from a single sensor.

In the following disclosure, various exemplary embodiments of the present invention are recited. One will understand that these examples are provided only for the sake of clarity and explanation and do not limit or otherwise confine the invention to the disclosed examples.

Figure 1A:
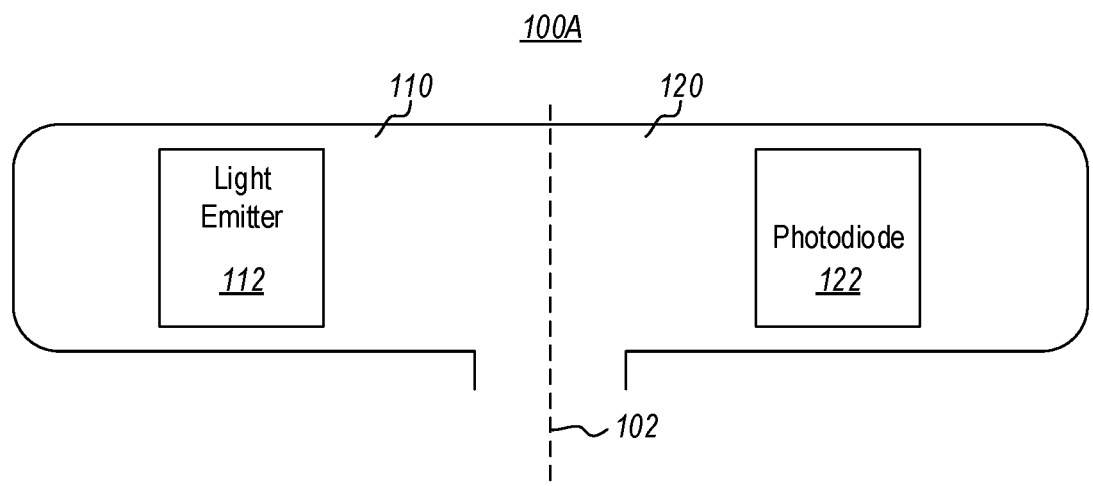
FIG. 1A illustrates an embodiment of a transmissive biometric sensor.

Notably, two separate types of photonic sensors have typically been used to measure biometric information (e.g., heart rate, blood oxygen saturation, blood carbon monoxide saturation, blood flow rate, relative hydration levels, and so forth) with respect to humans, transmissive sensors and reflective sensors. For example, FIG. 1A illustrates a transmissive probe topology shown by transmissive sensor (or probe) 100A. The transmissive sensor 100A may include two sides (i.e., side 110 and side 120) as shown being separated by a dashed-line 102. In particular, the transmissive sensor 100A may be folded around human tissue (e.g., a finger, a foot, and so forth) along the dashed-line 102. For instance, the transmissive sensor 100A may comprise a flexible printed circuit board (PCB) that is folded about the dashed-line 102. As shown, the transmissive sensor 100 also includes a light emitter 112 on the side 110 and a photodiode 122 on the side 120. More specifically, with respect to the transmissive probe topology, the light emitter 112 is placed on one side (e.g., the side 110) of human tissue where a measurement is to be taken, while the photodiode 122 is placed on the opposite side (e.g., the side 120) of the tissue. Accordingly, the emitter 112 is configured to emit light that passes from one side of the tissue through to the other side where the light is then measured by the photodiode 122.

Figure 1B:
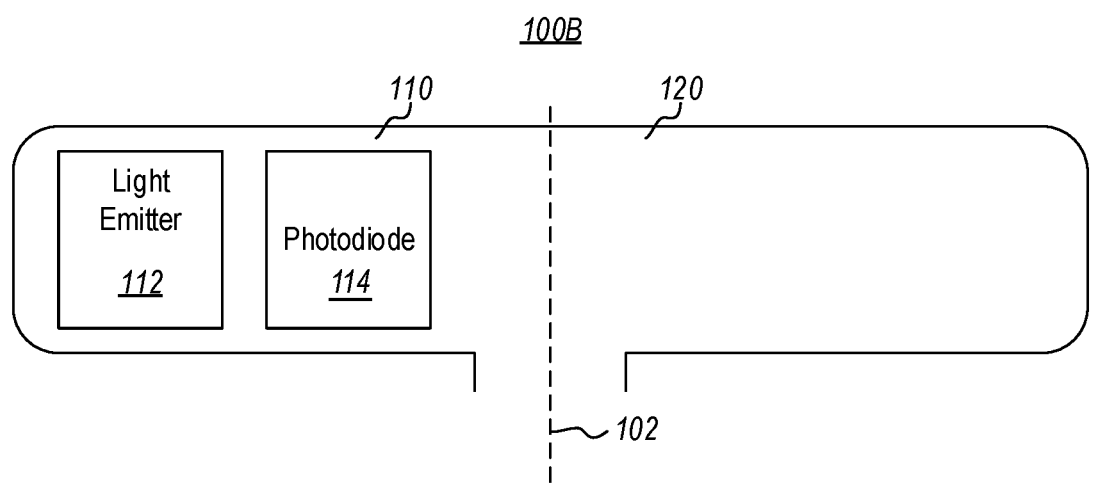
FIG. 1B illustrates another embodiment of a reflective biometric sensor.

FIG. 1B illustrates the second type of photonic sensor, a reflective sensor 100B. Again, the reflective sensor 100B may include two sides (i.e., side 110 and side 120), as shown being separated by dashed-line 102. However, with respect to the reflective probe topology, the light emitter 112 and a photodiode 114 are placed on the same side of the tissue (e.g., the side 110). As such, the light produced by the emitter 112 shines into the tissue resulting in a certain amount of light that is back scattered and hits the photodiode 114 after passing into the tissue and bouncing back out. The photodiode may then perform a measurement of the reflected light. Notably, while only one light emitter (e.g., the light emitter 112) and one photodiode (e.g., the photodiode 122 or the photodiode 114) are illustrated in both FIG. 1A and FIG. 1B, any number of light emitters and photodiodes may be used to practice the principles described herein.

While both the transmissive topology (i.e., illustrated by FIG. 1A) and the reflective topology (i.e., illustrated by FIG. 1B) have their advantages and disadvantages in a wide variety of monitoring scenarios, existing probe designs use one topology or the other. Thus, a user is forced to accept the advantages and disadvantages that come with a chosen topology. Accordingly, embodiments described herein include a sensor probe design having both a transmissive topology and a reflective topology.

Figure 2A:
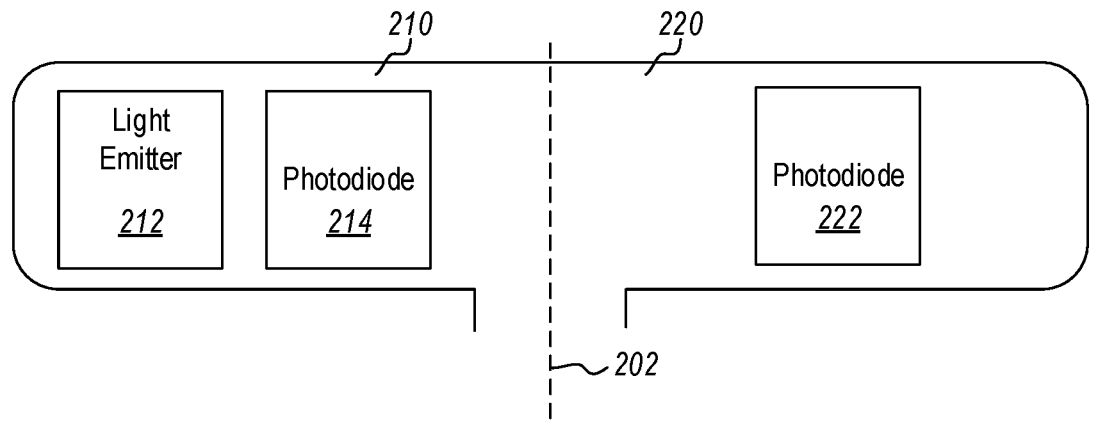
FIG. 2A illustrates an embodiment of a biometric sensor that includes both a transmissive topology and a reflective topology.

For instance, FIG. 2A illustrates an embodiment of a multi-purpose sensor probe design 200A that includes both topologies (i.e., a transmissive topology and a reflective topology). Once again, the multi-purpose sensor 200A may include two sides (i.e., side 210 and side 220) as shown being separated by a dashed-line 202. As discussed with respect to the transmissive sensor 100A and the reflective sensor 100B, the multi-purpose sensor 200A may also be folded around human tissue (e.g., a finger, a foot, and so forth) along the dashed-line 202.

As shown, the multi-purpose sensor 200A includes a light emitter 212 on the side 210 and a photodiode 222 on the side 220, which allows the multi-purpose sensor to function as a transmissive sensor (e.g., the transmissive sensor 100A). More specifically, the emitter 212 can emit light that passes from one side of tissue through to the other side where the light is then measured by the photodiode 222. Furthermore, the multi-purpose sensor 200A includes a photodiode 214 that is placed on the same side of the tissue (e.g., the side 210) as the light emitter 212, thus allowing the multi-purpose sensor to also function as a reflective sensor (e.g., the reflective sensor 100B). More specifically, the light produced by the emitter 210 may shine into tissue resulting in a certain amount of light that is back scattered and hits the photodiode 214 after passing into the tissue and bouncing back out. The photodiode 214 may then perform a measurement of the reflected light.

Accordingly, the multi-purpose sensor 200A may include components that allow for performing measurements using either or both of a transmissive topology and a reflective topology, as further described herein. Notably, while only one light emitter 212 is illustrated in FIG. 2A, any number of light emitters may be included. For instance, a separate photodiode may be used for the transmissive topology and the reflective topology of the multi-purpose sensor 200A (i.e., a first light emitter is used with the photodiode 222 in a transmissive topology and a second light emitter is used with the photodiode 214 in a reflective topology).

Figure 2B:
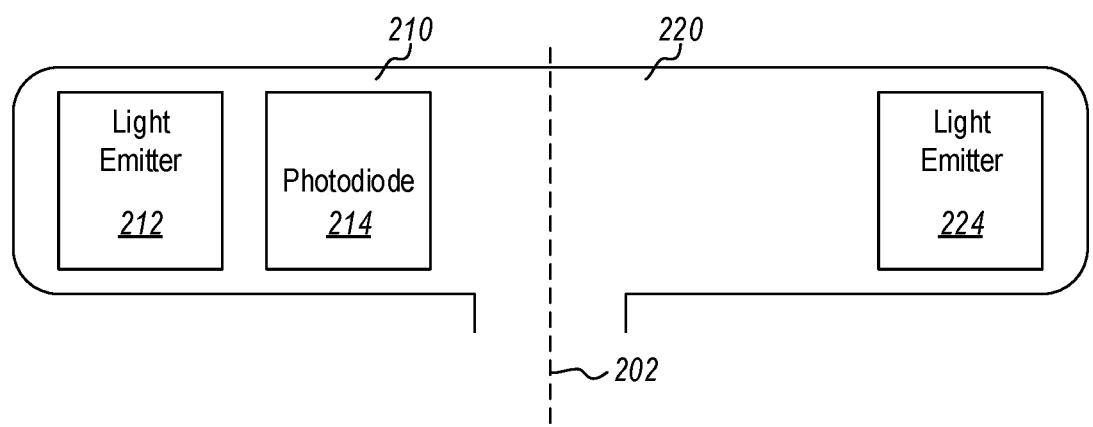
FIG. 2B illustrates another embodiment of a biometric sensor that includes both a transmissive topology and a reflective topology.

In an alternative multi-purpose sensor design, FIG. 2B illustrates the multi-purpose sensor 200B. As shown, the multi-purpose sensor 200B includes both topologies (i.e., a transmissive topology and a reflective topology). However, instead of using two photodiodes as illustrated by FIG. 2A (and the multi-purpose sensor 200A), the multi-purpose sensor 200B includes two light emitters (i.e., light emitter 212 and light emitter 224) with a single photodiode 214. More specifically, utilizing a transmissive topology, the light emitter 224 may produce light that passes from one side of tissue through to the other side where the light is then measure by the photodiode 214. Accordingly, utilizing a reflective topology, the light emitter 212 may produce light that is reflected back after entering tissue, which light is then measured by the photodiode 214.

Figure 3:
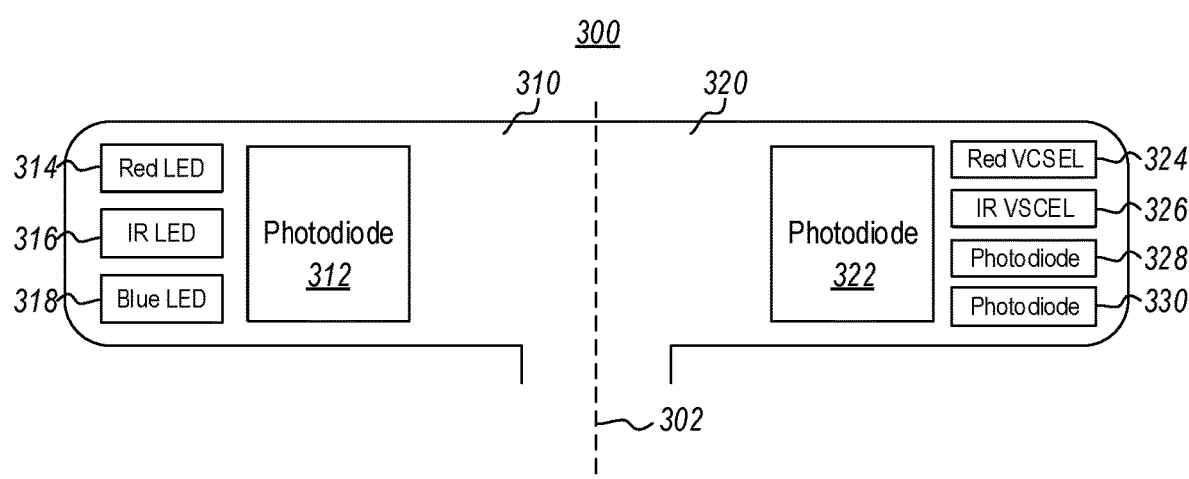
FIG. 3 illustrates another embodiment of a biometric sensor that includes both a transmissive topology and a reflective topology.

FIG. 3 illustrates a more specific example design of a multi-purpose sensor 300 that can be used to measure heart rate, blood oxygen saturation, blood carbon monoxide saturation, blood flow rate, and relative hydration levels. Additionally, the multi-purpose sensor 300 includes a transmissive topology and a reflective topology that can use either light-emitting diodes (LED's) or vertical-cavity surface-emitting lasers (VCSEL's) as light emitting sources. As illustrated, the multi-purpose sensor 300 includes a side 310 and a side 320 that are separated by dashed-line 302, a photodiode 312, a photodiode 322, a photodiode 328, a photodiode 330, a red LED 314, an infrared (ID) LED 316, a blue LED 318, a red VCSEL 324, and an IR VCSEL 326.

In a particular example, the multi-purpose sensor 300 may comprise a flexible PCB. In such an example, the photodiodes (i.e., the photodiode 312, the photodiode 322, the photodiode 328, and the photodiode 330) and light emitters (i.e., the red LED 314, the IR LED 316, the blue LED 318, the red VCSEL 324, and the IR VCSEL 326) may be soldered onto the flexible PCB. The flexible PCB may then be folded about dashed-line 302 around tissue (e.g., a foot or a finger) where measurements are to be taken. In such an example, the multi-purpose sensor may also include any appropriate circuitry that is configured to both control the light emitting sources (i.e., the red LED 314, the IR LED 316, the blue LED 318, the red VCSEL 324, and the IR VCSEL 326) either independently or simultaneously and capture analog measurements from the photodiodes (i.e., the photodiode 312, the photodiode 322, the photodiode 328, and the photodiode 330) either independently or simultaneously.

With the PCB folded about the tissue at the dashed-line 302, the multi-purpose sensor 300 may be used in either a transmissive or reflective photonics measurement topology. Notably, the multi-purpose sensor 300 includes four possible topology/emitter combinations: 1. transmissive-LED's, 2. reflective-LED's, 3. transmissive-VCSEL's, and 4. reflective VCSEL's. The transmissive-LED's combination may be utilized by driving the red LED 314 and the IR LED 316, while measurements are captured at the photodiode 322. The reflective-LED's combination may be utilized by driving the red LED 314 and the IR LED 316, while measurements are captured at the photodiode 312. The transmissive-VCSEL's combination may be utilized by driving the VCSEL's (i.e., the red VCSEL 324 and the IR VCSEL 326), while capturing measurements at the photodiode 312. Finally, the reflective-VCSEL's combination may be utilized by driving the VCSEL's (i.e., the red VCSEL 324 and the IR VCSEL 326), while measurements are captured by the photodiode 322. Notably, while the VCSEL's (i.e., the red VCSEL 324 and the IR VCSEL 326) is shown as being on the side 320 and the LED's (e.g., the red LED 314 and the IR LED 316) are shown as being on the opposite side (i.e., the side 310), VCSEL's and LED's may be included on the same side or included on both sides (i.e., VCSEL's and LED's both on the side 310 and the side 320).

As illustrated, the multi-purpose sensor (e.g., the multi-purpose sensor 300) may be capable of performing multiple types of measurements. For instance, the photodiode 312 may be used to measure heart rate when the IR LED 316 (i.e., reflective topology) or the IR VCSEL 326 (i.e., transmissive topology) is turned on. Similarly, the photodiode 322 may be used to measure heart rate when the IR LED 316 (i.e., transmissive topology) or the IR VCSEL 326 (i.e., reflective topology) is turned on. Additionally, the photodiode 312 may be used to measure blood oxygen saturation when the red LED 314 and the IR LED 316 (i.e., reflective topology) or the red VCSEL 324 and the IR VCSEL 326 (i.e., transmissive topology) are turned on. Similarly, the photodiode 322 may be used to measure blood oxygen saturation when the Red LED 314 and the IR LED 316 (i.e., transmissive topology) or the red VCSEL 324 and the IR VCSEL 326 (i.e., reflective topology) are turned on.

Blood carbon monoxide saturation may also be measured by the photodiode 312 (i.e., reflective topology) and the photodiode 322 (i.e., reflective topology) when the Blue LED is turned on. Furthermore, the photodiode 312 and the photodiode 322 may be sampled simultaneously, one in the reflective topology and the other in the transmissive topology, to acquire relative hydration levels. Finally, the photodiode 328 and the photodiode 330 may be simultaneously sampled while the red VCSEL 324 is turned on to measure blood flow rates.

Using any of the previous examples, heart rate, blood oxygen saturation, and so forth, measurements may be captured by the multi-purpose sensor (e.g., the multi-purpose sensor 200A, the multi-purpose sensor 300, and so forth) using one or both of a transmissive topology or a reflective topology. Accordingly, the multi-purpose sensors described herein may allow for utilizing both a transmissive topology and a reflective topology that can each capture measurements separately. Such multiple topology utilization may allow for determining accuracy of measurements, accuracy of particular topologies, and so forth. Additionally, the multi-purpose sensors described herein may allow for dynamically changing from one topology (e.g., a transmissive topology) to another topology (e.g., a reflective topology). Notably, dynamic topology switching may occur in response to user input (e.g., a user has indicated a desire to switch to a different topology) or based on a current measuring scenario (e.g., the sensor automatically switches to a different topology when a current measuring scenario dictates that another topology is more suitable for the current measuring scenario than the current topology). Again, allowing such dynamic topology switching may allow for determining accuracy, efficiency, and so forth corresponding to a given topology with respect to a current measurement scenario (i.e., current distance of light emitters from photodiodes, orientation of components, and so forth).

Furthermore, as described with respect to FIG. 3 (and the multi-purpose sensor 300), multiple types of light emitter sources may be utilized with respect to a single sensor. Notably, while LED's are the most common light emitter source used, in particular measurement scenarios, VCSEL's may offer advantages over LED's. For example, VCSEL's can often provide an ultra-low power, highly efficient emitter when strong optical coupling between a light emitter and a photodiode is present. Thus, VCSEL's may be preferable to LED's in circumstances that include strong optical coupling. However, beam angles associated with VCSEL's may be rather tight, which may result in poor VCSEL performance when circumstances include weak optical coupling. Accordingly, in the weak optical coupling scenario, LED's (which have a broader beam angle than VCSEL's) may be used to improve optical coupling and thereby increase the likelihood of capturing a legitimate measurement.

Notably, several factors may be present in determining a strength of optical coupling. For instance, such factors may include physical alignment, orientation, and/or distance between a given light emitter and a given photodiode. As such, photocoupling may change drastically between measurement sessions due to sensor placement or even during a measurement session due to a shifting probe. Accordingly, the multi-purpose sensors discussed with respect to FIG. 2 and FIG. 3 may allow for dynamically switching between LED's and VCSEL's as a given light emitting source on demand. Notably, dynamic light emitting source switching may occur in response to user input (e.g., a user has indicated a desire to switch to a different light emitting source) or based on a current measuring scenario (e.g., the sensor automatically switches to a different type of light emitting source when a current measuring scenario dictates that another type of light emitting source is more suitable for the current measuring scenario than the current light emitting source). Such switching may allow for using the most efficient and/or the most dependable light emitting source in any given monitoring scenario.

In this way, a multi-purpose sensor may include both a transmissive topology and a reflective topology in a single probe. The multi-purpose sensor may be configured to allow for dynamically switching from a first topology (e.g., a transmissive topology) to a second topology (e.g., a reflective topology) in accordance with a most suitable topology for a current scenario. The multi-purpose sensor may be further configured to measure multiple biometric signals from a single sensor probe. Furthermore, the described multi-purpose sensor is configured to allow for dynamically switching between different types of light emitting sources based on current measuring scenarios.

Although the subject matter has been described in language specific to structural features and/or methodological acts, it is to be understood that the subject matter defined in the appended claims is not necessarily limited to the described features or acts described above, or the order of the acts described above. Rather, the described features and acts are disclosed as example forms of implementing the claims.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A medical sensor for detecting blood oxygen saturation levels comprising:
   one or more light emitters;
   one or more photodiodes;
   circuitry configured to operate the one or more light emitters and the one or more photodiodes in a first configuration, the first configuration comprising a reflective topology and configured to detect blood oxygen saturation levels; and
   the circuitry is further configured to operate the one or more light emitters and the one or more photodiodes in a second configuration, the second configuration comprising a transmissive topology and configured to detect blood oxygen saturation levels;
   wherein:
      the circuitry is further configured to sample simultaneously from both the first configuration and the second configuration, and
      the circuitry is further configured to switch from the first configuration to the second configuration in response to user input.

2. The medical sensor of claim 1, wherein the circuitry is further configured to switch from the first configuration to the second configuration in response to a current measuring scenario.

3. A medical sensor for detecting blood oxygen saturation levels comprising:
   at least one light-emitting diode (LED) and at least one vertical-cavity surface-emitting laser (VCSEL), each of the at least one LED and each of the at least one VCSEL being configured to produce light, wherein each of the at least one LED and the at least one VCSEL can be individually activated to produce light; and
   at least two photodiodes that are configured to capture measurements associated with light produced by at least one of the at least one LED or the at least one VCSEL, wherein the at least one LED, the at least one VCSEL, and the at least two photodiodes are configurable to create both a transmissive topology and a reflective topology, both the transmissive topology and the reflective topology being configured to detect blood oxygen saturation levels and the at least two photodiodes configured to sample simultaneously from the reflective topology and the transmissive topology,
   wherein the medical sensor comprises circuitry that is configured to switch from the reflective topology to the transmissive topology in response to user input.

4. The medical sensor of claim 1, wherein a first photodiode selected from the one or more photodiodes is configured for use in both the transmissive topology and the reflective topology.

5. The medical sensor of claim 1, wherein a first photodiode selected from the one or more photodiodes is configured for use in the transmissive topology and a second photodiode selected from the one or more photodiodes is configured for use in the reflective topology.

6. The medical sensor of claim 1, further comprising:
   a first photodiode selected from the one or more photodiodes;
   a second photodiode selected from the one or more photodiodes;
   a third photodiode selected from the one or more photodiodes;
   a fourth photodiode selected from the one or more photodiodes;
   a red LED selected from the one or more light emitters;
   an infrared LED selected from the one or more light emitters;
   a blue LED selected from the one or more light emitters;
   a red VCSEL selected from the one or more light emitters; and
   an infrared VCSEL selected from the one or more light emitters.

7. The medical sensor of claim 6, wherein the medical sensor is further configured to control the red LED, the infrared LED, the blue LED, the red VCSEL, and the infrared VCSEL either independently or simultaneously.

8. The medical sensor of claim 7, wherein the medical sensor is further configured to capture measurements from the first photodiode, the second photodiode, the third photodiode, and the fourth photodiode either independently or simultaneously.

* * * * *